United States Patent [19]
McClellan et al.

[11] 3,987,107
[45] Oct. 19, 1976

[54] CONVERSION OF METHANOL TO FORMALDEHYDE

[75] Inventors: William R. McClellan, Kennett Square, Pa.; Alvin B. Stiles, Wilmington, Del.

[73] Assignee: E. I. Du Pont de Nemours and Company, Wilmington, Del.

[22] Filed: May 5, 1971

[21] Appl. No.: 140,590

Related U.S. Application Data

[62] Division of Ser. No. 805,016, March 6, 1969, Pat. No. 3,640,900.

[52] U.S. Cl. ............................ 260/603 HF; 252/436; 252/469
[51] Int. Cl.² ........................................ C07C 45/16
[58] Field of Search .............. 260/603 HF; 252/436, 252/469

[56] References Cited
UNITED STATES PATENTS

| | | |
|---|---|---|
| 2,462,413 | 2/1949 | Meath .......................... 260/603 HF |
| 2,519,788 | 8/1950 | Payne .......................... 260/603 HF |
| 3,497,461 | 2/1970 | McClellan et al. ........... 260/603 HF |
| 3,640,900 | 2/1972 | McClellan et al. ........... 260/603 HF |

FOREIGN PATENTS OR APPLICATIONS 577,573   5/1946   United Kingdom................ 260/606

*Primary Examiner*—Joseph E. Evans

[57] ABSTRACT

Methanol is converted to formaldehyde in a two step vapor phase process. In the first step the methanol is partially converted to formaldehyde over a silver catalyst, and in the second step the remaining methanol is converted to formaldehyde over a bismuth molybdate- or bismuth phosphomolybdate-on-titania catalyst having the formula:

$$Bi_aP_bMo_{12}(Ti_{1-x}Si_x)_cO_d$$

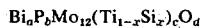

where $a$ is equal to or greater than 4, $b$ is 0 to 2, $c$ is 6 to 80, $d$ is $1.5a + 2.5b + 36 + 2c$ and $x$ is 0 to 0.5.

2 Claims, No Drawings

CONVERSION OF METHANOL TO FORMALDEHYDE

GROSS REFERENCE TO RELATED APPLICATIONS

This application is a divisional application of our copending application Ser. No. 805,016, filed Mar. 6, 1969, now U.S. Pat. No. 3,640,900.

BACKGROUND OF THE INVENTION

The invention relates to the use of heat-treated bismuth molybdate- and bismuth phosphomolybdate-on-colloidal titania catalysts for the preparation of formaldehyde.

Bismuth molybdate and phosphomolybdate catalysts are known in the art. They have been used for the oxidation of methanol and hydrocarbons, oxidative dehydrogenation of olefins, and also for the oxidation of olefin-ammonia mixtures to unsaturated nitriles.

Bismuth molybdate and phosphomolybdate catalysts are often deposited on a support. In general, silica is disclosed in the art as the preferred support. There are teachings that other materials which are inert may be used as alternate or auxiliary supports. For example, in U.S. Pat. No. 3,186,955, it is disclosed that "A preferred support is silica . . . Many other materials such as alundum, silicon carbide, aluminasilica, alumina, titania and other chemically inert materials may be employed as a support."

Bismuth molybdate and phosphomolybdate-on-silica catalysts may be prepared through use of silica sols, for example, see U.S. Pat. Nos. 3,248,340 and 2,904,580, though, more generally, the supported catalysts are prepared by impregnation of preformed solid inert supports with aqueous solutions of the active catalyst components. Although there are other methods of preparing supported catalysts, to applicants' knowledge, there is no specific description in the art of the preparation of bismuth molybdate-on-colloidal titania catalysts by use of titania sols.

U.S. Pat. No. 3,415,886 discloses calcining colloidal silica supported bismuth molybdate and phosphomolybdate catalysts, of the type described in U.S. Pat. No. 3,248,340 and 2,904,580, at 750°–850° C. to obtain compositions with improved selectivity and directivity in vapor phase oxidations. Further, these treated catalysts that have been heated at 750°–850° C. function, for vapor phase oxidations, at higher temperatures than is the case for the normally calcined product.

SUMMARY OF THE INVENTION

In parent application Ser. No. 805,016, filed Mar. 6, 1969, now U.S. Pat. No. 3,640,900, are described catalytic compositions of improved selectivity and directivity for vapor phase oxidations having the formula $Bi_aP_b\-Mo_{12}(Ti_{1-x}Si_x)_cO_d$, where $x = 0$ to $0.5$ and $a \geq 4$, $b = 0$ to $2$, $c = 6$ to $80$, and $d = 1.5a + 2.5b + 36 + 2c$. These catalytic compositions are obtained by mixing an aqueous titania sol and, optionally, an aqueous silica sol, with a composition containing bismuth oxide, molybdenum oxide, and, optionally, phosphorus oxide in said proportions, or a composition yielding such oxides. Optionally ammonium hydroxide or an ammonium carbonate is then added to the composition until the pH of the composite is in the range of 5.0 to 7.5. The composition is then dried and the resulting solid calcined at a temperature above 600° C. but below 700° C., preferably at 625°–675° C.

These titania supported catalysts show outstanding selectivity as catalysts in certain vapor phase oxidations, particularly in the oxidation of methanol to formaldehyde.

DETAILED DESCRIPTION OF THE INVENTION

The bismuth molybdate or phosphomolybdate-on-titania catalyst compositions useful in the process of the invention are described in detail in application Ser. No. 805,016, filed Mar. 6, 1969, now U.S. Pat. No. 3,640,900. The description and Examples of these catalysts and the manner of making them is herein incorporated by reference.

These novel bismuth molybdate and phosphomolybdate-on-titania catalysts give exceptionally high conversion and selectivity in the oxidation of methanol to formaldehyde.

These catalysts are particularly useful in a two-step process for the catalytic conversion of methanol to formaldehyde as set forth in Payne, U.S. Pat. No. 2,519,788. In this art process a mixture of methanol, air and steam is introduced into a converter containing a silver gauze catalyst. In the initial feed, the air to methanol weight ratio ranges from 0.5:1 to 2:1. In this converter the methanol is partially (65 to 80%) oxidized and dehydrogenated to formaldehyde. This reaction takes place between 300° and 850° C.

The reaction products from the first converter, which include unreacted methanol, formaldehyde, water vapor and by-products, are then cooled below 180° C. and introduced into a second converter. Prior to introduction, auxiliary air is added to the reaction products to provide additional oxygen. The second converter contains a metal oxide catalyst, e.g., molybdenum oxide, a metal phosphate catalyst promoted with molybdic oxide, or an iron molybdate catalyst. In this converter the unconverted methanol is oxidized to formaldehyde. This second converter operates at a temperature between 250° and 600° C., and the oxygen concentration is between 7 and 14 volume per cent.

The just described process is considerably improved by using catalysts of the present invention in the second stage or converter in lieu of the art metal oxide catalyst.

Use of the catalyst of the present invention permits wider ranges of temperature, greater variation in methanol and oxygen concentration, and also permits the addition of methanol with the supplementary air. It is usually satisfactory to employ an amount of oxygen 15–150% greater than the theoretical amount needed to convert the methanol to water and formaldehyde.

The maximum amount of methanol that can be used without encountering runaway reaction in a process of the type described in U.S. Pat. No. 2,519,788 is at least 10% greater when the present catalyst is employed in the second converter. This additional methanol can be added with the auxiliary air introduced into the product stream from the first converter and the capacity of a given commercial unit can be increased by a minimum expenditure for new facilities.

The present catalyst has the additional valuable property of resistance to fusion and/or loss of catalytic activity under runaway reaction conditions. The infrequent, but almost certain runaway reaction encountered in the second stage converter with the commercial catalysts usually employed requires shutdown of the unit for laborious removal of fused catalyst. The present catalyst survives runaway reaction temperatures greater than 650° C. without loss of catalytic activity.

The following examples are offered to further illustrate the catalysts of this invention. All amounts are expressed in parts by weight unless otherwise indicated.

EXAMPLE I

To 270 parts of a titania sol containing 13% by weight $TiO_2$ is added a solution of 84 parts of $Bi(NO_3)_3 \cdot 5H_2O$ dissolved in 43 parts of water containing 3.5 parts of 70% nitric acid. With stirring, a solution of 41 parts of $(NH_4)_6Mo_7O_{24} \cdot 4H_2O$ in 46 parts of water and then 1.5 parts of 85% phosphoric acid is added, and the resulting slurry is adjusted to a pH of 6.4 by the addition of 30 parts of ammonium carbonate. Stirring is continued until gelation occurs. The gel is dried in an oven at 110° C. and then calcined in a furnace at 450° C. for 20 hours. After cooling, the product is screened to 8–14 mesh size. Catalyst (10 ml.) prepared by heating the calcined product at 650° C. for 2 hours has the following analyses; Ti, 19.21%; Bi, 34.18%; Mo, 19.68%; P, 0.5%; 0 (by difference) 26.43%. These data correspond to a composition (based on $Mo_{12}$): $Bi_{9.2}P_{1.0}Mo_{12}Ti_{23.4}O_{98.4}$.

This catalyst is useful in the second stage of a two stage conversion of methanol to formaldehyde, using a silver catalyst in the first stage.

EXAMPLE II

A catalyst is prepared as described in Example I except that 150 parts of a 12.5% by weight $TiO_2$ sol and 2.5 parts of 85% by weight of phosphoric acid solutions are used in place of the amounts of the respective components specified in Example I. The final calcined product is heated at 650° C. for 3 hours.

A side-stream reactor consisting of a stainless steel tube 1 inch in diameter, which contains 15 cc. of this catalyst and which is immersed in a circulating salt bath as a heat exchange medium, is connected into the line between the primary (silver gauze catalyst) and secondary (iron molybdate catalyst) converters in a commercial methanol oxidation process. First stage reaction product consisting of 7.8% $O_2$, 7.2% methanol, 17% formaldehyde, 7.5% hydrogen, 0.6% CO, 1.5% $CO_2$, 10.6% water, and 47.8% nitrogen is passed into the side-stream reactor tube at a rate of 1500 cc./min. The heat exchange bath is controlled at a temperature of 335° C. Analysis of the reaction product shows essentially quantitative conversion (> 99.8%) of methanol at 86.5% overall yield of formaldehyde.

In a control experiment for the above Example, 15 cc. of commercial iron molybdate catalyst is tested under the same conditions. A conversion of > 99.8% is obtained with a heat exchange bath temperature of 305° C. and the yield of formaldehyde is 80%.

In another control experiment, a catalyst is prepared just as described above using silica sol in place of titania sol. This catalyst is calcined at 450° C. and a portion of it is further heated at 650° C. for 3 hours. The 450° C. calcined bismuth phosphomolybdate-on-silica catalyst under the same conditions described above gives an 82% yield of formaldehyde with a heat exchange bath temperature of 300° C. The 650° C. treated bismuth phosphomolybdate-on-silica catalyst gives lower conversions of methanol at slightly higher selectivity.

What is claimed is:

1. In a two-step process for the vapor phase conversion of methanol with oxygen to formaldehyde, wherein the first step a portion of the methanol is converted over a silver catalyst, the improvement comprising converting at a temperature between 250° and 600° C, the remainder of the methanol in the second step over a bismuth molybdate-on-titania catalyst formed by admixing with an aqueous titania sol a bismuth compound, a molybdenum compound and optionally a phosphorus compound or a silicon compound in proportions which, after drying the admixture and calcining the dried admixture at a temperature and calcining the dried admixture at a temperature above 600° C but below 700° C, correspond to the formula

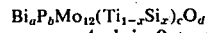

$Bi_aP_bMo_{12}(Ti_{1-x}Si_x)_cO_d$ where $a \geq 4$, $b$ is 0 to 2, $c$ is 6 to 80, $d$ is $1.5a + 2.5b + 36 + 2c$, and $x$ is 0 to 0.5, and the atomic ratio of bismuth to molybdenum does not exceed about 3:1.

2. The two-step process of claim 1 wherein additional methanol is added to the reaction product of the first step prior to being fed into the second step.

* * * * *